US008617305B2

(12) United States Patent
Lei et al.

(10) Patent No.: US 8,617,305 B2
(45) Date of Patent: Dec. 31, 2013

(54) METAL COMPLEXES FOR METAL-CONTAINING FILM DEPOSITION

(75) Inventors: Xinjian Lei, Vista, CA (US); Daniel P. Spence, Carlsbad, CA (US)

(73) Assignee: Air Products and Chemicals, Inc., Allentown, PA (US)

( * ) Notice: Subject to any disclaimer, the term of this patent is extended or adjusted under 35 U.S.C. 154(b) by 50 days.

(21) Appl. No.: 13/348,228

(22) Filed: Jan. 11, 2012

(65) Prior Publication Data

US 2013/0008345 A1    Jan. 10, 2013

Related U.S. Application Data

(60) Provisional application No. 61/436,000, filed on Jan. 25, 2011.

(51) Int. Cl.
| | |
|---|---|
| C07F 5/00 | (2006.01) |
| C09D 1/00 | (2006.01) |
| C23C 16/06 | (2006.01) |
| C23C 16/40 | (2006.01) |
| C23C 16/513 | (2006.01) |
| C07C 251/04 | (2006.01) |
| C07C 211/00 | (2006.01) |
| C07F 15/00 | (2006.01) |
| C07F 7/00 | (2006.01) |
| C07F 7/28 | (2006.01) |

(52) U.S. Cl.
USPC ............ 106/286.2; 556/32; 556/51; 556/138; 106/287.18; 106/287.19; 427/255.31; 427/569; 427/255.28; 564/248

(58) Field of Classification Search
None
See application file for complete search history.

(56) References Cited

U.S. PATENT DOCUMENTS

| 5,782,986 | A | 7/1998 | Butterbaugh et al. |
|---|---|---|---|
| 5,820,664 | A | 10/1998 | Gardiner et al. |
| 6,620,971 | B2 | 9/2003 | Chang et al. |
| 6,752,869 | B2 | 6/2004 | Lee et al. |
| 7,132,556 | B2 | 11/2006 | Benvenuti et al. |
| 7,691,984 | B2 | 4/2010 | Lei et al. |
| 7,723,493 | B2 | 5/2010 | Lei et al. |
| 2005/0170092 | A1 | 8/2005 | Benvenuti et al. |
| 2006/0258173 | A1 | 11/2006 | Xiao et al. |
| 2007/0248754 | A1 | 10/2007 | Lei et al. |
| 2008/0032062 | A1 | 2/2008 | Meiere |
| 2009/0136685 | A1* | 5/2009 | Lei et al. .................. 427/576 |
| 2009/0302434 | A1 | 12/2009 | Pallem et al. |
| 2010/0078601 | A1 | 4/2010 | Pallem et al. |

FOREIGN PATENT DOCUMENTS

| EP | 369297 | B1 | 8/1993 |
|---|---|---|---|
| EP | 1227079 | A2 | 7/2002 |
| EP | 1 273 683 | A2 | 1/2003 |
| EP | 1 676 849 | A | 7/2006 |
| EP | 1 676 850 | A | 7/2006 |
| EP | 1 676 850 | A1 | 7/2006 |
| EP | 1 849 789 | A1 | 10/2007 |
| JP | 02-188564 | A | 7/1990 |
| JP | 03-163055 | A | 7/1991 |
| JP | 3227891 | A1 | 10/1991 |
| JP | 6-298714 | A | 10/1994 |
| JP | 6298714 | A2 | 10/1994 |
| JP | 08-259528 | A | 10/1996 |
| JP | 2000-503805 | A | 3/2000 |
| JP | 2002-193988 | A | 7/2002 |
| JP | 2002-302473 | A | 10/2002 |
| JP | 2002-338590 | A2 | 11/2002 |
| JP | 2004-014813 | A | 1/2004 |
| JP | 2005-531619 | A | 10/2005 |
| KR | 10-2009-0007099 | A | 4/2007 |
| KR | 10-2009-0007102 | A | 4/2007 |
| TW | 200403249 | B | 3/2004 |
| TW | I256078 | | 6/2006 |
| TW | I256078 | B | 6/2006 |
| WO | 02/18394 | A1 | 3/2002 |
| WO | 02/018394 | A1 | 3/2002 |
| WO | 2004002946 | A1 | 1/2004 |

OTHER PUBLICATIONS

Edelmann, F.T.; "Lanthanide Amidinates and Guanidinates: from Laboratory Curiosities to Efficient Homogeneous Catalysts and Precursors for Rare-Earth Oxide Thin Films"; The Royal Society of Cehmistry; vol. 38; 2009; pp. 2253-2268.
Husekova, K., et al.; "Preparation of High Permittivity GdScO3 Films by Liquid Injection MOCVD"; EXC Transactions; vol. 25, No. 8; 2009; pp. 1061-1064.
Jones, A.C., et al.; "Recent Developments in the MOCVD and ALD of Rare Earth Oxides and Silicates"; Materials Science and Engineering; vol. 118; 2005; pp. 97-104.
Katamreddy, R., et al.; "Atomic Layer Deposition of Rare-Earth Oxide Thin Films for High-k Dielectric Applications"; ECS Transactions; vol. 19, No. 2; 2009; pp. 525-536.
Mao, L., et al.; "Syntheses of {(MeC5H4)2Ln(THF)[O—CN(i-Pr)2—NPh]} (Ln ) Y, Er, Yb) and the X-ray Crystal Structure of the Yttrium Complex: The Active Species for Polymerization of Phenyl Isocyanate by (Diisopropylamido) bis(methylcyclopentadienyl)lanthanides"; Organometallics; vol. 16; 1997; pp. 3711-3714.
Nief, F., et al.; "Heterocyclopentadienyl Complexes of Group-3 Metals"; Eur. J. Inorg. Chem.; 2001; pp. 891-904.
Paivasaari, J., et al.; "Synthesis, structure and properties of volatile lanthanide complexes containing amidinate ligands: application for Er2O3 thin film growth by atomic layer deposition"; J. Mater. Chem.; vol. 15; 2005; pp. 4224-4233.

(Continued)

*Primary Examiner* — Yun Qian
(74) *Attorney, Agent, or Firm* — Rosaleen P. Morris-Oskanian

(57) ABSTRACT

Novel families of tri-valent metal complexes including scandium, yttrium, lanthanum, cerium, praseodymium, neodymium, samarium, europium, gadolinium, terbium, dysprosium, holmium, erbium, thulium, ytterbium, lutetium, aluminum, gallium, indium, manganese, antimony, bismuth; and of divalent metal complexes including magnesium, calcium, strontium, barium, manganese, cobalt, iron, nickel, ruthenium, copper, zinc, cadium are disclosed. These metal complexes can be used as precursors to deposit metal or metal oxide films in semi-conductor industries.

15 Claims, 3 Drawing Sheets

(56) References Cited

OTHER PUBLICATIONS

Peng, H., et al.; "Synthesis, Reactivity, and Characterization of Sodium and Rare-Earth Metal Complexes Bearing a Dianionic N-Aryloxo-Functionalized B-Ketoiminate Ligand"; Inorg. Chem.; vol. 47; 2008; pp. 9828-9835.
Wilkinson, G., et al.; Steroids. LXIII. Synthesis of A4-19-Norpregnene-11B,17x, 21-Triol-3,20 Dione (19-Norhydrocortisone) and Related 19-Noradrenal Hormones; J. Am. Chem. Soc.; vol. 76, No. 23; 1954; p. 6210.
Matthews, et al.; Chemical Vapor Deposition; vol. 6, No. 3; 2000; pp. 129-132.
Chou, Tsung-Yi, Synthesis and Characterization of Tris(B-ketoimlnato)ruthenium(III) Complexes: Potential Precursors for CVD of Ru and RuO2 Thin Films, Chemical Vapor Deposition, 2004, pp. 149-158, vol. 10 No. 3.
Matthews, J.S., et al; 'CVD of MgO from a Mg(B-ketoiminate)2: Preparation, Characterization, and Utilization of an Intramolecularly Stabilized, Highly Volatile, Thermally Robust Precursor; Chemical Vapor Deposition; vol. 6, No. 3; 2000; pp. 129-132.
Edwards D.A., et al; "Aerosol-Assisted Chemical Vapour Deposition (AACVD) of Silver Films from Triphyenylphospine Adducts of Silver .Beta.-diketonates and .Beta.-diketoiminates, Including the Structure of [Ag(hfac)(PPh3)]"; Journal of Materials Chemistry; vol. 9, No. 8; 1999; pp. 1771-1780; XP002372344.
Bouquillon S, et al; "Simultaneous Generation of Anionic and Neutral Palladium(II) Complexes from Eta3-Allylpalladium Chloride Dimer and Fluorinated Beta-Enaminones"; European Journal of Organic Chemistry; No. 24; 2003; pp. 4714-4720; XP002372342.
Tung Y-L, et al; "Synthesis and Characterization of Allyl(Beta-Ketoiminato)Palladium (II) Complexes: New Precursors for Chemical Vapor Deposition of Palladium Thin Films"; Organometallics; vol. 18, No. 5; Feb. 5, 1999; pp. 864-869; XP002372343.
Collier W, et al; "Kinetics of Acid Hydrolysis of Nickel(II) and Copper(II) Compounds with the Cyclic Diamines 1,5-Diazocane, and 4,4-Dimethyl-7-(5,5,7-Trim Ethyl-1,4-Diazepan-1-Yl)-5-Azaheptan-2-Ol"; Australian Journal of Chemistry; vol. 42, No. 9;1989; pp. 1611-1616; XP009089097.
Douglas L Schulz, et al, New Precursors for Barium MOCVD, Inorg. Chem., 1993, 249-250, 32, 3, Amer. Chem. Soc.
Sergej Pasko, et al, Synthesis and Characterization of New Alkaline Earth Metal B-ketoiminates. Inorg. Chem., 2005, 483-487, 8, Elsevier B.V.
Pier Luigi Franceschini, et al, Volatile B-Ketoiminato- and B-Diketiminator-Based Zirconium Complexes as Potential MOCVD Precursors, Inorg. Chem., 2003, 7273-7282, 42, Amer. Chem. Soc.
Tsung-Yi Chou, et al, Synthesis and Characterization of Tris (B-ketoiminator) ruthenium(III) Complexes: . . . Chem. Vap. Deposition, 2004, 10, 3, 149-158.
Sunkwon Lim, et al, A Study on the Development of Chemical Vapor Deposition Precursors. 4. Synthesis and . . . Chem. Mater., 2002, 14, 1548-1554, Amer. Chem. Soc.
Sunkwon Lim, et al, A Study on the Development of CVD Precursors V—synthesis and Characterization of new N-alkoxy-B-ketoiminate Comlexes of Titanium, Jour. Organ. Chem., 2004, 689, 224-237, Elsevier B.V.
Nikki L. Edleman, et al, Synthesis and Characterization of Volatile, Fluorine-Free B-Ketoiminate Lanthanide MOCVD Precursors and Their Implementation in . . . Inorg. Chem., 2002, 41, 5005-5023, Amer. Chem. Soc.
Studebaker Daniel B., et al, "Encapsulating Bis(B-Ketoiminator) Polyethers, Volatile, Fluorine-Free Barium Precursors for Metal . . . ", Inorg. Chem., 2000, 39, 3148-3157, Amer. Chem. Soc.
Matthews Jason S., et al, "Group 2 Element Precursors for the Chemical Vapor Deposition of Electronic Materials", Adv. In Inorg. Chem., 50, 2000, 173-192, Academic Press.
Loeb S.J., et al., "Coordination Modes of Polydentate Ligands. 2. Template Synthesis of Four-, Five-, and Six-Coordinate Fluorinated Schiff-Base Complexes of Ni2+: Structure of an Octahedral Ni2+ Complex Containing Two Tridentate Ligands", Inorganic Chemistry, vol. 23, 1984, 1509-1512.

Becht, M., et al, "117. Synthesis Crystal Structure and Thermal Behaviour of Some New Copper Complexes with Tridentate B-lminoketone Ligands", Helvetica Chimica Acta, 1994, vol. 77(5), 1288-1298.
Collier W, et al; "Kinetics of Acid Hydrolysis of Nickel(II) and Copper(II) Compounds with the Cyclic Diamines 1,5-Diazocane, and 4,4-Dimethyl-7-(5,5,7-Trim Ethyl-1,4-Diazepan-1-Yl)-5-Azaheptan-2-Ol"; Australian Journal of Chemistry; vol. 42, No. 9; 1989; pp. 1611-1616; XP009089097.
Konefal E, et al; "Coordination Modes of Polydentate Ligands. 1. Template Synthesis of Complexes of Nickel(2+), Copper(2+), and Cobalt(2+) with Pentadentate and Hexadentate Ligands: Structure of a Highly Distorted Six Coordinate Cobalt(2+) Complex"; Inorganic Chemistry; vol. 23, No. 5; 1984; pp. 538-545; XP009079427.
Curtis N.F., et al; "Preparations, Magnetic Susceptibility and Structural Studies of Trinuclear Copper(II) Compounds of 4,4,9,9-Tetramethyl-5,8-Diazadodecane-2,11-Diol"; Australian Journal of Chemistry; vol. 41, No. 10; 1988; pp. 1545-1555; XP009089095.
Morgan, K.R., et al; "Preparation, and Complexes with Nickel(II) and Copper(II), of a Diazepane Amine Alcohol. The Structure of [4,4-Dimethyl-7-(5,5,7-Trimethyl-1,4-Diazepan-1-Yl)-5-Azaheptan-2-Ol]Nickel (II) Perchlorate"; Austrailian Journal of Chemistry; vol. 36, No. 7; 1983; pp. 1341-1351; XP009089096.
Martin J.W.L., et al; "Fluorinated Alkoxides. Part XIII. The Reduction of Beta-Imino-Alkoxy Complexes to give Stable, Polydentate, Amino Alcohols"; Canadian Journal of Chemistry; vol. 56, No. 23;1978; pp. 2966-2969; XP009089101.
Konefal E., et al; "Coordination Modes of Polydentate Ligands. 1. Template Synthesis of Complexes of Nickel(2+), Copper(2+), and Cobalt(2+) with Pentadentate and Hexadentate Ligands: Structure of a Highly Distorted Six-Coordinate Cobalt(2+) Complex"; Inorganic Chemistry; vol. 23, No. 5; 1984; pp. 538-545; XP009079427.
Curtis N. F., et al; "Preparations, Magnetic Susceptibility and Structural Studies of Trinuclear Copper(II) Compounds of 4,4,9,9-Tetramethyl-5,8-Diazadodecane-2,11-Diol"; Australian Journal of Chemistry; vol. 41, No. 10; 1988; pp. 1545-1555; XP009089095.
Martin J.W.L., et al; "Fluorinated Alkoxides. Part XIII. The Reduction of Beta-Imino-Alkoxy Complexes to give Stable, Polydentate, Amino Alcohols"; Canadian Journal of Chemistry; vol. 56, No. 23; 1978; pp. 2966-2969; XP009089101.
Schulz Douglas L., et al, "New Precursors for Barium MOCVD", Inorg. Chem., 1993, 249-250, 32 3, Amer. Chem. Soc.
Pasko Sergej, et al, "Synthesis and Characterization of New Alkaline Earth Metal B-ketoiminates", Inorg. Chem., 2005, 483-487, 8, Elsevier B.V.
Franceschini Pier Luigi, et al, Volatile B-Ketoiminato- and B-Diketiminator-Based Zirconium Complexes as Potential MOCVD Precursors, Inorg. Chem., 2003, 7273-7282, 41, Amer. Chem. Soc.
Chou Tsung-Yi, et al, "Synthesis and Characterization of Tris (B-ketoiminator) ruthenium (III) Complexes: . . . ", Chem. Vap. Deposition, 2004, 10, 3, 149-158.
Lim Sunkwon, et al, "A Study on the Development of Chemical Vapor Deposition Precursors. 4. Synthesis and . . . ", Chem. Mater., 2002, 14, 1548-1554, Amer. Chem. Soc.
Lim Sunkwon, et al, "A Study on the Development of CVD Precursors V—synthesis and Characterization of new N-alkoxy-B-ketoiminate Complexes of Titanium", Jour. Organ. Chem., 2004, 689, 224-237, Elsevier B.V.
Edelman Nikki L., et al, "Synthesis and Characterization of Volatile, Fluorine-Free B-Ketoiminate Lanthanide MOCVD Precursors and Their Implementation in . . . ", Inorg. Chem., 2002, 41, 5005-5023, Amer. Chem. Soc.
Edleman, Nikki L., Synthesis and Characterization of Volatile, Fluorine-Free B-Ketoiminate Lanthanide MOCVD Precursors and Their Implementation in Low-Temperature Growth of Epitaxial CeO2 Buffer Layers for Superconducting Electronics, Inorganic Chemistry, 2002, pp. 5005-5023, vol. 41.
Lim, Sunkwon, A Study on the Development of CVD Precursors V—syntheses and Characterization of New N-alkoxy-B-ketoiminate Complexes of Titanium, Journal of Organometallic Chemistry, 2004, pp. 224-237, vol. 689.
Lim, Sunkwon, A Study on the Development of Chemical Vapor Deposition Precursors. 4. Syntheses and Characterization of New

(56) References Cited

OTHER PUBLICATIONS

N-Alkoxo-B-ketoiminate Complexes of Niobium and Tantalum, Chemical Material, 2002, pp. 1548-1554, vol. 14.

Matthews, Jason S., CVD of MgO from a Mg(B-ketoiminate)2: Preparation Characterization, and Utilization of an Intramolecularly Stabilized, Highly Volatile, Thermally Robust Precursor, Chemical Vapor Deposition, 2000, pp. 129-132, vol. 6, No. 3.

Ouattara T. S., Synthesis and Characterization of bis[4-N-(cyclohexylimino)-2-pentanonato]magnesium(II), Journal of Coordination Chemistry, 2005, pp. 461-465, vol. 58, No. 5.

Pasko, Sergej., Synthesis and Characterization of New Alkaline Earth Metal B-ketoiminates. The First Structurally Characterized Strontium B-ketoiminate, Inorganic Chemistry Communications, 2005, pp. 483-487, vol. 8.

Schulz, Douglas L., New Precursors for Barium MOCVD. B-Ketoiminate Complexes Containing Appended Polyether "Lariats", Inorganic Chemistry, 1993, pp. 249-250, vol. 32.

Yun, Chi, Ph.D.; "Design, Synthesis and Application of a New Chemical Vapor Deposition Precursor"; Chemistry Research Institute; Oct. 2004; Doctoral Dissertation; pp. 1-17.

* cited by examiner

METAL COMPLEXES FOR METAL-CONTAINING FILM DEPOSITION

CROSS REFERENCE TO RELATED APPLICATION

The present patent application claims the benefit of U.S. Provisional Patent Application Ser. No. 61/436,000, filed Jan. 25, 2011.

BACKGROUND OF THE INVENTION

The semiconductor industry is currently considering the use of thin metal or metal containing films for a variety of applications. Many organometallic complexes have been evaluated as potential precursors for the formation of these thin films.

U.S. Patent Application Publication No. US2009302434A and WO09149372A disclose methods and compositions for depositing rare earth metal-containing layers. In general the disclosed methods deposit the precursor compounds comprising rare earth metal-containing compounds using deposition methods such as chemical vapor deposition or atomic layer deposition. The disclosed precursor compounds include a cyclopentadienyl ligand having at least one aliphatic group as a substituent and an amidine ligand.

The tutorial review by Edelmann, F. T. "Lanthanide Amidinates and Guanidinates: From Laboratory Curiosities to Efficient Homogeneous Catalysts and Precursors for Rare-Earth Oxide Thin Films." Chemical Society Reviews 38(8): 2253-2268 (2009) teaches that a hot topic in current organolanthanide chemistry is the search for alternative ligand sets which are able to satisfy the coordination requirements of the large lanthanide cations. Among the most successful approaches in this field is the use of amidinate ligands of the general type [RC(NR')$_2$]$^-$ (R=H, alkyl, aryl; R'=alkyl, cycloalkyl, aryl, SiMe$_3$) which can be regarded as steric cyclopentadienyl equivalents. Closely related are the guanidinate anions of the general type [R$_2$NC(NR')$_2$]$^-$ (R=alkyl, SiMe$_3$; R'=alkyl, cycloalkyl, aryl, SiMe$_3$). Two amidinate or guanidinate ligands can coordinate to a lanthanide ion to form a metallocene-like coordination environment which allows the isolation and characterization of stable though very reactive amide, alkyl, and hydride species. Mono- and trisubstituted lanthanide amidinate and guanidinate complexes are also readily available. Various rare earth amidinates and guanidinates have turned out to be very efficient homogeneous catalysts e.g. for ring-opening polymerization reactions. Moreover, certain alkyl-substituted lanthanide tris(amidinates) and tris(guanidinates) were found to be highly volatile and could thus be promising precursors for ALD (=Atomic Layer Deposition) and MOCVD (=Metal-Organic Chemical Vapor Deposition) processes in materials science and nanotechnology. This tutorial review covered the success story of lanthanide amidinates and guanidinates and their transition from mere laboratory curiosities to efficient homogeneous catalysts as well as ALD and MOCVD precursors.

Husekova, K., M. JurkoviC, K. Cico, D. Machajdik, E. DobroCka, R. Luptak, A. Mackova and K. Frohlich "Preparation of High Permittivity GdScO$_3$ Films by Liquid Injection MOCVD." ECS Transactions 25(8): 1061-1064 (2009) teach the preparation and properties of GdScO$_3$ thin films. The films were prepared by liquid injection metal-organic chemical vapor deposition, MOCVD at 600° C. on (100) Si substrate. The as-deposited films were amorphous with a smooth surface and sharp GdScO$_3$/Si interface. X-ray diffraction showed that the amorphous phase is well preserved upon rapid thermal annealing up to 1000° C. However, modification of the X-ray reflectivity pattern after annealing at 1000° C. indicates increasing of the film thickness, presumably due to diffusion of silicon from the substrate into the whole volume of the film. Capacitance-voltage measurement resulted in dielectric constant of 22. It is shown, that exact stoichiometry of GdScO$_3$ is not necessary to achieve dielectric constant above 20.

Jones, A. C., H. C. Aspinall, P. R. Chalker, R. J. Potter, K. Kukli, A. Rahtu, M. Ritala and M. Leskela "Recent Developments in The MOCVD and ALD of Rare Earth Oxides and Silicates." Materials Science and Engineering B 118(1-3): 97-104 (2005) investigate lanthanide, or rare-earth as alternatives to SiO$_2$ as the dielectric insulating layer in sub-0.1 µm CMOS technology. Metalorganic chemical vapour deposition (MOCVD) and atomic layer deposition (ALD) are promising techniques for the deposition of these high-K dielectric oxides and in this paper some of our recent research into the MOCVD and ALD of PrO$_x$, La$_2$O$_3$, Gd$_2$O$_3$, Nd$_2$O$_3$ and their related silicates are reviewed.

Japanese patent application No, JP2002338590 A2 discloses 11 tris(ethylcyclopentadienyl)lanthanides represented by general formula Ln(C$_5$H$_4$Et)$_3$ (Ln=La, Pr, Nd, Sm, Gd, Tb, Dy, Ho, Er, Tm, Yb, Lu, Y) are prepared by reaction of anhydrous lanthanide chloride with ethylcyclopentadienyl potassium in THF or an inert organic solvent containing THF, removing a salt formed and distilling off unreacted reactants, THF, solvent, and byproducts under reduced pressure, and vacuum distillation to recover the product.

Katamreddy, R., N. A. Stafford, L. Guerin, B. Feist, C. Dussarrat, V. Pallem, C. Weiland and R. Opila "Atomic Layer Deposition of Rare-Earth Oxide Thin Films for High-K Dielectric Applications" ECS Transactions, 19(2): 525-536 (2009) propose many different organolanthanide molecules as metal sources for depositing metal and metal oxide layers for semiconductors by atomic layer deposition (ALD). These precursors needed particular physical and thermal properties to be used in the semiconductor manufacturing process. For example, the precursors needed to have high volatility, reactivity, and thermal stability. ALD deposition methods were very promising; however, new high-K metal oxide films would require new precursors to meet the very stringent requirements of the semiconductor process. Tris(cyclopentadienyl) rare earth compounds are interesting for use as precursors because of their high vapor pressures, often low melting points and availability in the liquid state, high reactivity towards water, and high growth rates for deposition. In this study, the various important thermal properties of Cp-based lanthanide precursors along with their ALD properties for metal oxide deposition were studied.

U.S. Patent Application Publication No. US20080032062A1 discloses organometallic compounds represented by the formula M(NR1R2)x wherein M is a metal or metalloid, R1 is the same or different and is a hydrocarbon group or a heteroatom-containing group, R2 is the same or different and is a hydrocarbon group or a heteroatom-containing group; R1 and R2 can be combined to form a substituted or unsubstituted, saturated or unsaturated cyclic group; R1 or R2 of one (NR1R2) group can be combined with R1 or R2 of another (NR1R2) group to form a substituted or unsubstituted, saturated or unsaturated cyclic group; x is equal to the oxidation state of M; and wherein said organometallic compound has (i) a steric bulk sufficient to maintain a monomeric structure and a coordination number equal to the oxidation state of M with respect to anionic ligands, and (ii) a molecular weight sufficient to possess a volatility suitable for vapor deposition; a process for producing the organometallic compounds, and a method for producing a film or coating from organometallic precursor compounds.

Nief, F. "Heterocyclopentadienyl Complexes of Group-3 Metals." European Journal of Inorganic Chemistry(4): 891-904 (2001) teaches that heterocyclopentadienyl complexes of group-3 metals (scandium, yttrium, lanthanum and the lanthanides, and uranium) are compounds in which one or more —CH units of a cyclopentadienyl-like ligand have been replaced by a heteroelement (nitrogen, phosphorus, arsenic, or antimony). These ligands can have very diverse substitution patterns, notably with bridged and cavitand-like structures. In addition to the classical $\eta^5$-coordination behaviour, the heterocyclopentadienyl ligand can adopt a very large array of coordination patterns. Some complexes have a very promising chemistry since they have been found to activate small molecules such as nitrogen and ethylene.

Päiväsaari, J. and I. Charles L. Dezelah, Dwayne Back, Hani M. El-Kaderi, Mary Jane Heeg, Matti Putkonen, Lauri Niinistö and Charles H. Winter "Synthesis, structure and properties of volatile lanthanide complexes containing amidinate ligands: application for $Er_2O_3$ thin film growth by atomic layer deposition." J. Mater. Chem. 15: 4224-4233 (2005) teach the treatment of anhydrous rare earth chlorides with three equivalents of lithium 1,3-di-tert-butylacetamidinate (prepared in situ from the di-tert-butylcarbodiimide and methyllithium) in tetrahydrofuran at ambient temperature afforded $Ln(^tBuNC(CH_3)N^tBu)_3$ (Ln=Y, La, Ce, Nd, Eu, Er, Lu) in 57-72% isolated yields. X-Ray crystal structures of these complexes demonstrated monomeric formulations with distorted octahedral geometry about the lanthanide(III) ions. These new complexes are thermally stable at >300° C., and sublime without decomposition between 180-220° C./0.05 Torr. The atomic layer deposition of $Er_2O_3$ films was demonstrated using $Er(^tBuNC(CH_3)N^tBu)_3$ and ozone with substrate temperatures between 225-300° C. The growth rate increased linearly with substrate temperature from 0.37 Å per cycle at 225° C. to 0.55 Å per cycle at 300° C. Substrate temperatures of >300° C. resulted in significant thickness gradients across the substrates, suggesting thermal decomposition of the precursor. The film growth rate increased slightly with an erbium precursor pulse length between 1.0 and 3.0 s, with growth rates of 0.39 and 0.51 Å per cycle, respectively. In a series of films deposited at 250° C., the growth rates varied linearly with the number of deposition cycles. Time of flight elastic recoil analyses demonstrated slightly oxygen-rich $Er_2O_3$ films, with carbon, hydrogen and fluorine levels of 1.0-1.9, 1.7-1.9 and 0.3-1.3 atom %, respectively, at substrate temperatures of 250 and 300° C. Infrared spectroscopy showed the presence of carbonate, suggesting that the carbon and slight excess of oxygen in the films are due to this species. The as-deposited films were amorphous below 300° C., but showed reflections due to cubic $Er_2O_3$ at 300° C. Atomic force microscopy showed a root mean square surface roughness of 0.3 and 2.8 nm for films deposited at 250 and 300° C., respectively.

Peng, H., Z. Zhang, R. Qi, Y. Yao, Y. Zhang, Q. Shen and Y. Cheng "Synthesis, Reactivity, and Characterization of Sodium and Rare-Earth Metal Complexes Bearing a Dianionic N-Aryloxo-Functionalized β-ketoiminate Ligand." Inorganic Chemistry 47(21): 9828-9835 (2008) teach the synthesis and reactivity of a series of sodium and rare-earth metal complexes stabilized by a dianionic N-aryloxo-functionalized β-ketoiminate ligand. The reaction of acetylacetone with 1 equivalent of 2-amino-4-methylphenol in absolute ethanol gave the compound 4-(2-hydroxy-5-methylphenyl)imino-2-pentanone (LH2, 1) in high yield. Compound 1 reacted with excess NaH to afford the novel sodium cluster $[LNa_2(THF)_2]_4$ (2) in good isolated yield. Structure determination revealed that complex 2 has the 22-vertex cage structure. Reactions of complex 2 with anhydrous $LnCl_3$ in a 1:4 molar ratio, after workup, gave the desired lanthanide chlorides $[LLnCl(DME)]_2[Ln=Y$ (3), Yb (4), Tb (5)] as dimers. A further study revealed that complexes 3-5 are inert for chlorine substitution reactions. $(ArO)_3Ln$ (THF) $(ArO=2,6-Bu^t2-4-MeC_6H_2O)$ reacted with compound 1 in a 1:1 molar ratio in tetrahydrofuran (THF), after workup, to give the desired rare-earth metal aryloxides as dimers [LLn(OAr)(THF)]$_2$[Ln=Nd (6), Sm (7), Yb (8), Y (9)] in high isolated yields. All of these complexes are well characterized, and the definitive molecular structures of complexes 2 and 4-6 were determined. It was found that complexes 6-9 can be used as efficient initiators for L-lactide polymerization, and the ionic radii of the central metals have a significant effect on the catalytic activity.

U.S. Patent Application Publication No. US2010078601 teaches methods and compositions for depositing rare earth metal-containing layers. In general the disclosed methods deposit the precursor compounds comprising rare earth-containing compounds using vapor deposition methods such as chemical vapor deposition or atomic layer deposition. In certain embodiments the disclosed precursor compounds include a cyclopentadienyl ligand having at least one aliphatic group as a substituent.

A need still exists in the industry for developing new volatile, reactive, and thermally stable compounds as potential precursors to deposit metal containing films via chemical vapor deposition (CVD) and atomic layer deposition(ALD).

This invention is directed to a novel family of group 2 to 15 metal complexes which can be potentially used as precursors to deposit metal or metal oxide films in semi-conductor industries.

BRIEF SUMMARY OF THE INVENTION

One aspect of this invention is directed to metal containing complexes with structure I having both multidentate ketoimine and alkoxy or amino ligands

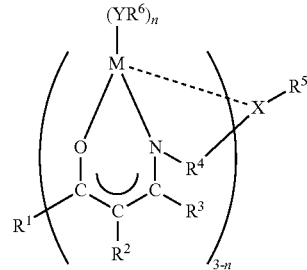

Structure I wherein M is selected from a tri-valent metal ions including scandium, yttrium, lanthanum, cerium, praseodymium, neodymium, samarium, europium, gadolinium, terbium, dysprosium, holmium, erbium, thulium, ytterbium, lutetium, aluminum, gallium, indium, manganese, antimony, bismuth; wherein $R^1$ is selected from the group consisting of linear or branched alkyl having from 1 to 10 carbon atoms; $R^2$ is selected from the group consisting of hydrogen, alkyl having from 1 to 10 carbon atoms, and aryl having 6 to 10 carbon atoms; $R^3$ is linear or branched selected from the group consisting of alkyl having 1 to 10 carbon atoms and aryl having 6 to 10 carbon atoms; $R^4$ is a linear or branched alkyl bridge having 2 to 10 carbon atoms; $R^{5-6}$ are individually selected from the group consisting of C1-10 linear or branched alkyl; n=1 or 2; $R^1$ and $R^2$ can be connected to form a cyclic group, preferably 5- or 6-membered ring; $R^4$ and $R^5$ can also be connected to form a cyclic group, preferably 5- or 6-membered ring; X is selected from O or NR' wherein R' is selected from the group consisting of C1-10 linear or branched alkyl or alkylsilyl having 3-10 carbon atoms; Y is selected from O or NR'' wherein R'' is selected from the group consisting of $C_{1-10}$ linear or branched alkyl or alkylsilyl having 3-10 carbon atoms.

Another aspect of this invention is directed to a family of metal-containing complexes with structure II having both multidentate ketoimine and alkoxy or amino ligands:

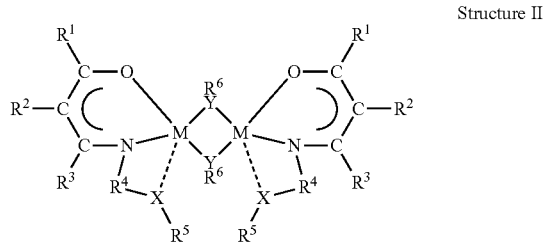

Structure II wherein M is a divalent metal ions including magnesium, calcium, strontium, barium, manganese, cobalt, iron, nickel, ruthenium, copper, zinc, cadium; wherein $R^1$ is selected from the group consisting of linear or branched alkyl having from 1 to 10 carbon atoms; $R^2$ is selected from the group consisting of hydrogen, alkyl having from 1 to 10 carbon atoms, and aryl having 6 to 10 carbon atoms; $R^3$ is linear or branched selected from the group consisting of alky having 1 to 10 carbon atoms and aryl having 6 to 10 carbon atoms; $R^4$ is a linear or branched alkyl bridge having 2 to 10 carbon atoms; $R^{5-6}$ are individually selected from the group consisting of consisting of $C_{1-10}$ alkyl, preferably $C_{1-3}$ alkyl; $R^1$ and $R^2$ can be connected to form a cyclic group, preferably 5- or 6-membered ring; $R^4$ and $R^5$ can also be connected to form a cyclic group, preferably 5- or 6-membered ring. X is selected from O or NR'' wherein R'' is selected from the group consisting of C1-10 linear or branched alkyl or alkylsilyl having 3-10 carbon atoms; Y is selected from O or NR'' wherein R'' is selected from the group consisting of C1-10 linear or branched alkyl or alkylsilyl having 3-10 carbon atoms.

Another aspect of this invention is directed to the methods for producing metal containing films, or multi-component metal oxide films via either a chemical vapor deposition (CVD), cyclic chemical vapor deposition (CCVD), plasma enhanced cyclic chemical vapor deposition (PECCVD), an atomic layer deposition(ALD), or plasma enhanced atomic layer deposition (PEALD), employing the metal containing complexes containing both multi-dentate ketoimine and alkoxy or amino ligands, having structure selected from the group consisting of structure I and structure II.

Yet, another aspect of this invention is directed to a multi-component metal oxide film by employing a precursor comprising at least one metal containing complex containing both multidentate ketoimine and alkoxy or amino ligands, having structure selected from the group consisting of structure I and structure II.

DETAILED DESCRIPTION OF THE INVENTION

Figure 1:
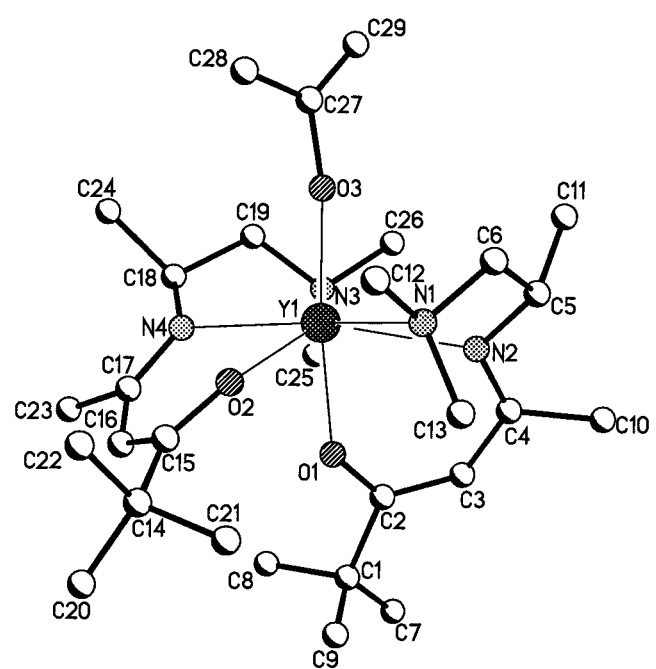
FIG. 1 Crystal structure of bis(2,2-dimethyl-5(1-dimethylamino-2-propylimino)-3-hexanonato-N,O,N')(iso-propoxy)yttrium FIG. 2 Thermogravimetric analysis (TGA) of bis(2,2-dimethyl-5(1-dimethylamino-2-propylimino)-3-hexanonato-N,O,N')(iso-propoxy)yttrium, demonstrating almost complete vaporization and suggesting it can be used as precursor to deposit yttrium-containing films.

The first embodiment of this invention discloses a class of metal containing complexes having both multi-dentate ketoimine and alkoxy or amino ligands represented by structure I shown below:

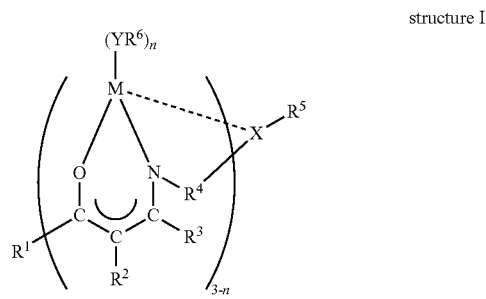

structure I wherein M is selected from a tri-valent metal ions including scandium, yttrium, lanthanum, cerium, praseodymium, neodymium, samarium, europium, gadolinium, terbium, dysprosium, holmium, erbium, thulium, ytterbium, lutetium, aluminum, gallium, indium, manganese, antimony, bismuth; wherein $R^1$ is selected from the group consisting of linear or branched alkyl having from 1 to 10 carbon atoms; $R^2$ can be from the group consisting of hydrogen, alkyl having from 1 to 10 carbon atoms, and aryl having 6 to 10 carbon atoms; $R^3$ is linear or branched selected from the group consisting of alkyl having 1 to 10 carbon atoms and aryl having 6 to 10 carbon atoms; $R^4$ is a linear or branched alkyl bridge having 2 to 10 carbon atoms; $R^{5-6}$ are individually selected from the group consisting of $C_{1-10}$ linear or branched alkyl; n=1 or 2; $R^1$ and $R^2$ can be connected to form a cyclic group, preferably 5- or 6-membered ring; $R^4$ and $R^5$ can also be connected to form a cyclic group, preferably 5- or 6-membered ring; X is selected from O or NR' wherein R' is selected from the group consisting of $C_{1-10}$ linear or branched alkyl or alkylsilyl having 3-10 carbon atoms; Y is selected from O or NR'' wherein R'' is selected from the group consisting of $C_{1-10}$ linear or branched alkyl or alkylsilyl having 3-10 carbon atoms.

The first example of the first embodiment of this invention is represented by the structure I(A) shown below:

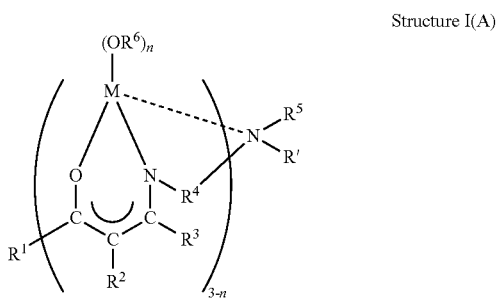

Structure I(A)

wherein $R^1$ is selected from the group consisting of linear or branched alkyl having from 1 to 5 carbon atoms; $R^2$ can be from the group consisting of hydrogen, methyl, and ethyl; $R^3$ is a linear or branched alkyl having 1 to 5 carbon atom; $R^4$ is a linear or branched alkyl bridge having 2 to 4 carbon atoms; $R^5$ and a are individually selected from the group consisting of C1-2 alkyl; and $R^6$ is selected from the group consisting of C1-5 linear or branched alkyl; and n=1 or 2; $R^1$ and $R^2$ can be connected to form a cyclic group; $R^4$ and $R^5$ can also be connected to form a cyclic group.

The second example of the first embodiment of this invention is represented by the structure I(B) shown below:

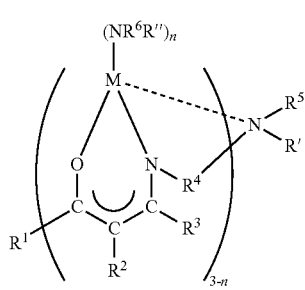

Structure I(B)

wherein $R^1$ is selected from the group consisting of linear or branched alkyl having from 1 to 5 carbon atoms; $R^2$ can be from the group consisting of hydrogen, methyl, and ethyl; $R^3$ is a linear or branched alkyl having 1 to 5 carbon atoms; $R^4$ is a linear or branched alkyl bridge having 2 to 4 carbon atoms; $R^5$ and a are individually selected from the group consisting of C1-2 alkyl; and $R^6$ and R" are individually selected from the group consisting of C1-5 linear or branched alkyl; n=1, 2; $R^1$ and $R^2$ can be connected to form a cyclic group; $R^4$ and $R^5$ can also be connected to form a cyclic group.

The third example of the first embodiment of this invention is represented by the structure I(C) shown below:

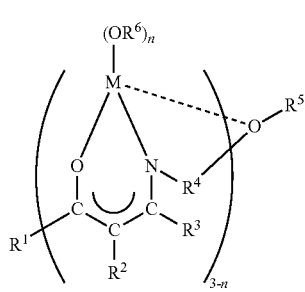

Structure I(C)

wherein $R^1$ is selected from the group consisting of linear or branched alkyl having from 1 to 5 carbon atoms; $R^2$ can be from the group consisting of hydrogen, methyl, and ethyl; $R^3$ is a linear or branched alkyl having 1 to 5 carbon atoms; $R^4$ is a linear or branched alkyl bridge having 2 to 4 carbon atoms; $R^5$ is selected from the group consisting of C1-2 alkyl; and $R^6$ is selected from the group consisting of $C_{1-5}$ linear or branched alkyl; n=1 or 2; $R^1$ and $R^2$ can be connected to form a cyclic group; $R^4$ and $R^5$ can also be connected to form a cyclic group.

The fourth example of the first embodiment of this invention is represented by the structure I(D) shown below:

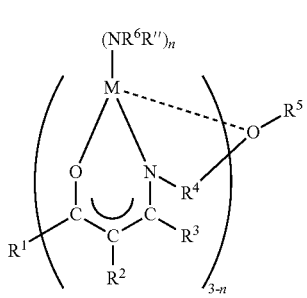

Structure I(D)

wherein $R^1$ is selected from the group consisting of linear or branched alkyl having from 1 to 5 carbon atoms; $R^2$ can be from the group consisting of hydrogen, methyl, and ethyl; $R^3$ is a linear or branched alkyl having 1 to 5 carbon atoms; $R^4$ is a linear or branched alkyl bridge having 2 to 4 carbon atoms; $R^5$ is selected from the group consisting of $C_{1-2}$ alkyl; and $R^6$ and R" are individually selected from the group consisting of $C_{1-5}$ linear or branched alkyl; and n=1 or 2; $R^1$ and $R^2$ can be connected to form a cyclic group; $R^4$ and $R^5$ can also be connected to form a cyclic group.

The second embodiment of this invention discloses a family of metal-containing complexes containing both multidentate ketoimine and alkoxy or amino ligands which is represented by the structure II shown below:

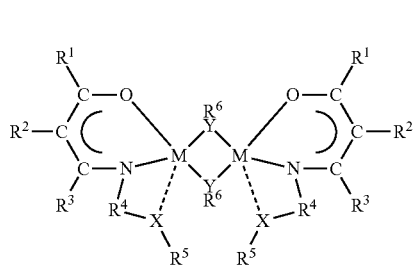

Structure II wherein M is a divalent metal ions including magnesium, calcium, strontium, barium, manganese, cobalt, iron, nickel, ruthenium, copper, zinc, cadium; wherein $R^1$ is selected from the group consisting of linear or branched alkyl having from 1 to 10 carbon atoms; $R^2$ can be from the group consisting of hydrogen, alkyl having from 1 to 10 carbon atoms, and aryl having 6 to 10 carbon atoms; $R^3$ is linear or branched selected from the group consisting of alky having 1 to 10 carbon atoms and aryl having 6 to 10 carbon atoms; $R^4$ is a linear or branched alkyl bridge having 2 to 10 carbon atoms; $R^{5-6}$ are individually selected from the group consisting of consisting of $C_{1-10}$ alkyl, preferably $C_{1-3}$alkyl; $R^7$ is selected from the group consisting of $C_{1-10}$ alkyl, preferably C1-3 $R^1$ and $R^2$ can be connected to form a cyclic group, preferably 5- or 6-membered ring; $R^4$ and $R^5$ can also be connected to form a cyclic group, preferably 5- or 6-membered ring. X is selected from O or NR' wherein R' is selected from the group consisting of $C_{1-10}$ linear or branched alkyl or alkylsilyl having 3-10 carbon atoms; Y is selected from O or NR" wherein R" is selected from the group consisting of $C_{1-10}$ linear or branched alkyl or alkylsilyl having 3-10 carbon atoms.

An example of the second embodiment of the invention is represented by the structure II(E) shown below:

Structure II(E)

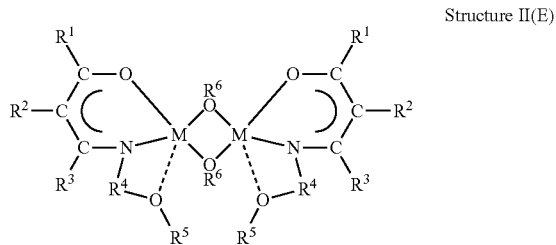

wherein $R^1$ is selected from the group consisting of linear or branched alkyl having from 1 to 5 carbon atoms; $R^2$ can be from the group consisting of hydrogen, methyl, and ethyl; $R^3$ is a linear or branched alkyl having 1 to 5 carbon atoms; $R^4$ is a linear or branched alkyl bridge having 2 to 4 carbon atoms; $R^5$ is selected from the group consisting of $C_{1-2}$ alkyl; $R^6$ is selected from the group consisting of $C_{1-5}$ linear or branched alkyl; $R^1$ and $R^2$ can be connected to form a cyclic group; $R^4$ and $R^5$ can also be connected to form a cyclic group.

Another example of the second embodiment of the invention is represented by the structure II(F) shown below Structure II(F)

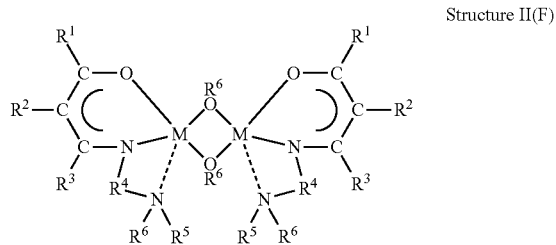

wherein $R^1$ is selected from the group consisting of linear or branched alkyl having from 1 to 5 carbon atoms; $R^2$ can be from the group consisting of hydrogen, methyl, and ethyl; $R^3$ is a linear or branched alkyl having 1 to 5 carbon atoms; $R^4$ is a linear or branched alkyl bridge having 2 to 4 carbon atoms; $R^5$ and R' are individually selected from the group consisting of C1-2 alkyl; and $R^6$ is selected from the group consisting of C1-5 linear or branched alkyl; $R^1$ and $R^2$ can be connected to form a cyclic group; $R^4$ and $R^5$ can also be connected to form a cyclic group.

The term "linear or branched alkyl" throughout the description denotes a hydrocarbon group having from 1 to 10 carbon atoms, preferably from 1 to 5 carbon atoms. Exemplary alkyl groups include, but are not limited to, methyl, ethyl, n-propyl, iso-propyl, n-butyl, iso-butyl, sec-butyl, tert-butyl, n-pentyl, isopentyl, tert-pentyl, hexyl, octyl, and decyl.

The term "cyclic group" throughout the description denotes a hydrocarbon or aromatic group having from 3 to 10 carbon atoms, preferably from 5 to 6 carbon atoms. Exemplary cyclic groups include, but are not limited to, 5- to 6-membered saturated hydrocarbon ring, 5- to 6-membered hydrocarbon unsaturated ring, and 5- to 6-membered aromatic ring.

These metal-containing complexes having both tridentate β-ketoiminate ligands and alkoxy or amino can be employed as potential precursors to make thin metal, metal oxide, or multi-component metal oxide films via either a chemical vapor deposition (CVD), cyclic chemical vapor deposition (CCVD), plasma enhanced cyclic chemical vapor deposition (PECCVD), an atomic layer deposition(ALD), or plasma enhanced atomic layer deposition (PEALD) method at temperatures less than 500° C. The CVD, CCVD, PECCVD, ALD or PEALD process can be carried out with or without reducing or oxidizing agents whereas an ALD process usually involves the employment of another reactant such as a reducing agent or oxidizing agent. The reducing agent can be selected from the group consisting of hydrogen, ammonia, hydrogen plasma, ammonia plasma, hydrogen/nitrogen plasma and their mixture thereof. The oxidizing agent can be selected from the group consisting of oxygen, ozone, water, oxygen plasma, water plasma, and their mixture thereof.

The multi-component metal oxide include but not limited to titanium doped yttrium oxide, titanium doped scandium oxide, titanium doped lanthanide (lanthanum, cerium, praseodymium, neodymium, samarium, europium, gadolinium, terbium, dysprosium, holmium, erbium, thulium, ytterbium, lutetium) oxides, hafnium doped yttrium oxide, hafnium doped scandium oxide, hafnium doped lanthanide (lanthanum, cerium, praseodymium, neodymium, samarium, europium, gadolinium, terbium, dysprosium, holmium, erbium, thulium, ytterbium, lutetium) oxides, zirconium doped yttrium oxide, zirconium doped scandium oxide, zirconium doped lanthanide (lanthanum, cerium, praseodymium, neodymium, samarium, europium, gadolinium, terbium, dysprosium, holmium, erbium, thulium, ytterbium, lutetium) oxides, and their mixture thereof.

For multi-component metal oxide, these complexes can be used in combination with other volatile metal precursors, or they can be premixed if they have the same tridentate β-ketoiminate ligands as well as alkoxy or amino ligands. These metal-containing complexes with tridentate β-ketoiminate ligands can be delivered in vapor phase into a CVD or ALD reactor via well-known bubbling or vapor draw techniques. A direct liquid delivery method can also be employed by dissolving the complexes in a suitable solvent or a solvent mixture to prepare a solution with a molar concentration from 0.001 to 2 M depending the solvent or mixed-solvents employed.

The solvent employed in solubilizing the precursor for use in a deposition process may comprise any compatible solvent or their mixture including aliphatic hydrocarbons, aromatic hydrocarbons, ethers, esters, nitrites, and alcohols. The solvent component of the solution preferably comprises a solvent selected from the group consisting of glyme solvents having from 1 to 20 ethoxy —$(C_2H_4O)$— repeat units; $C_2$-$C_{12}$ alkanols, organic ethers selected from the group consisting of dialkyl ethers comprising $C_1$-$C_6$ alkyl moieties, $C_4$-$C_8$ cyclic ethers; $C_{12}$-$C_{60}$ crown $O_4$-$O_{20}$ ethers wherein the prefixed $C_i$ range is the number i of carbon atoms in the ether compound and the suffixed $O_i$ range is the number i of oxygen atoms in the ether compound; $C_6$-$C_{12}$ aliphatic hydrocarbons; $C_6$-$C_{18}$ aromatic hydrocarbons; organic esters; organic amines, polyamines and organic amides.

Working Example

Example 1

Synthesis of Bis(2,2-dimethyl-5(1-dimethylamino-2-propylimino)-3-hexanonato-N,O,N)(iso-propoxy) yttrium To a solution of 2.00 g (7.51 mmol) yttrium(III)isopropoxide in 50 mL of THF at room temperature was added 3.40 g (15.03 mmol) 2,2-dimethyl-5(1-dimethylamino-2-propylimino)-3-hexanone in 25 mL of THF. Reaction mixture was refluxed for 16 hours after which volatiles were removed under vacuum. Isolated a grainy oil that was subjected to vacuum distillation to remove any excess ligand. Residual waxy solid was recrystallized in hexanes to yield large block-like crystals.

Elemental analysis: calcd for $C_{29}H_{57}N_4O_3Y$: C, 58.18; N, 9.36; H, 9.60. Found: C, 53.72; N, 9.11; H, 10.29. $^1H$ NMR (500 MHz, $C_6D_6$): δ=5.21 (s, 2H), 4.52 (septet, 1H), 3.77 (t, 2H), 3.42 (m, 2H), 2.51 (b, 6H), 1.97 (b, 6H), 1.80 (s, 6H), 1.75 (dd, 2H), 1.45 (dd, 6H), 1.30 (s, 18H), 1.10 (d, 6H).

The crystal structure of bis(2,2-dimethyl-5(1-dimethylamino-2-propylimino)-3-hexanonato-N,O,N')(iso-propoxy)yttrium was shown in FIG. 1.

Figure 2:
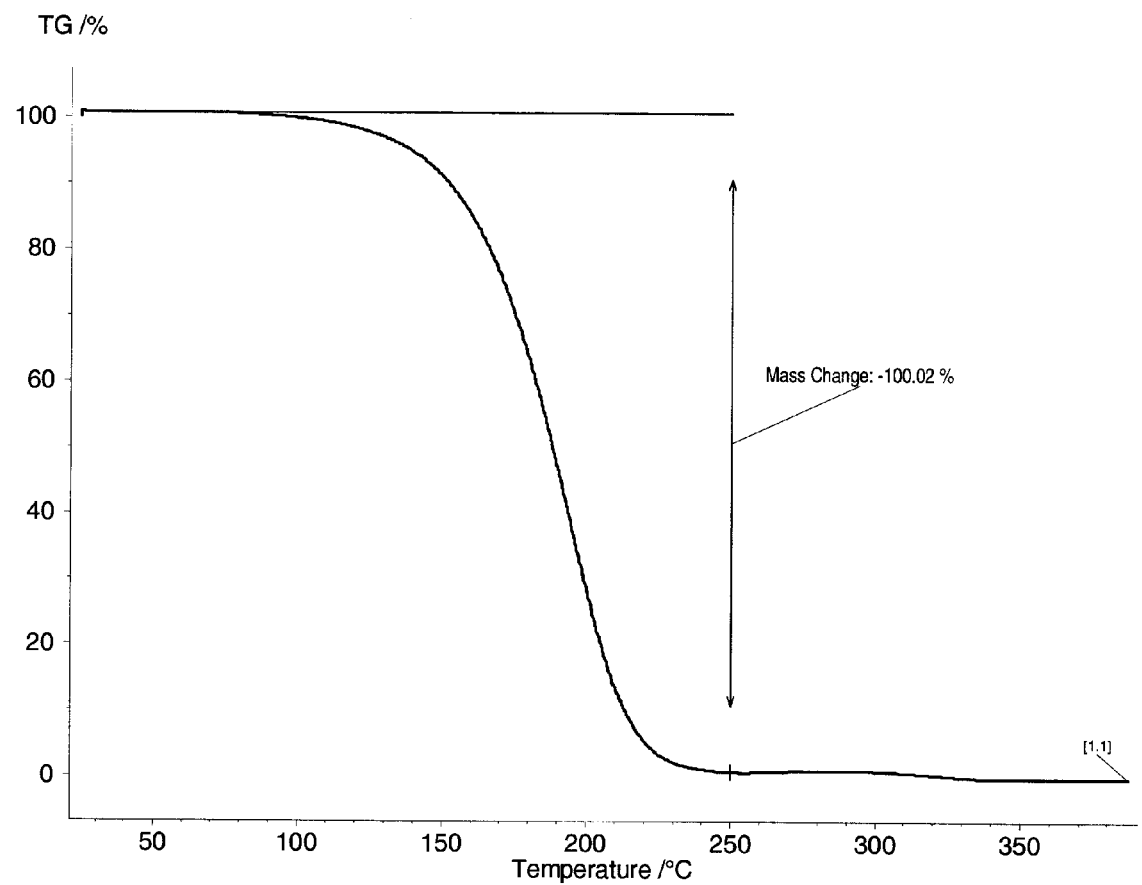

Thermal gravimetric analysis (TGA) of bis(2,2-dimethyl-5(1-dimethylamino-2-propylimino)-3-hexanonato-N,O,N')(iso-propoxy)yttrium was shown in FIG. 2. TGA showed the compound undergoes almost complete vaporization and suggested that bis(2,2-dimethyl-5(1-dimethylamino-2-propylimino)-3-hexanonato-N,O,N')(iso-propoxy)yttrium is thermally stable and can be used as precursor to deposit yttrium-containing films.

Bis(2,2-dimethyl-5(1-dimethylamino-2-propylimino)-3-hexanonato-N,O,N')(iso-propoxy)yttrium represented structure I(A) with M=yttrium, $R^1=Bu^t$, $R^2=H$, $R^3=Me$, $R^4=$—CH(Me)CH$_2$—, $R^5=R'=Me$, $R^6=Pr^i$, and n=1.

Example 2

Synthesis of (2,2-dimethyl-5(1-dimethylamino-2-propylimino)-3-hexanonato-N,O,N')(ethoxy)magnesium Dimer To a mixture of 0.25 g (10.28 mmol) magnesium turnings and 4.66 g (20.57 mmol) 2,2-dimethyl-5(1-dimethylamino-2-propylimino)-3-hexanone in 40 mL of toluene at room temperature was added 0.95 g (20.57 mmol) of anhydrous ethanol. Reaction mixture was refluxed for 16 hours after which it became a homogenous solution. Volatiles were removed under vacuum yielding an oil that was suspended into hexanes and heated into solution. Crystals were grown as a result.

Elemental analysis: calcd for $C_{30}H_{60}Mg_2N_4O_4$: C, 61.13; N, 9.50; H, 10.26. Found: C, 58.69; N, 9.44; H, 10.10. $^1$H NMR (500 MHz, $C_6D_6$): δ=5.17 (s, 2H), 4.08 (m, 2H), 3.99 (m, 2H), 3.19 (m, 2H), 3.06 (t, 2H), 2.21 (b, 12H), 1.78 (s, 6H), 1.78 (dd, 2H), 1.40 (s, 18H), 1.37 (t, 6H), 1.03 (d, 6H).

Figure 3:
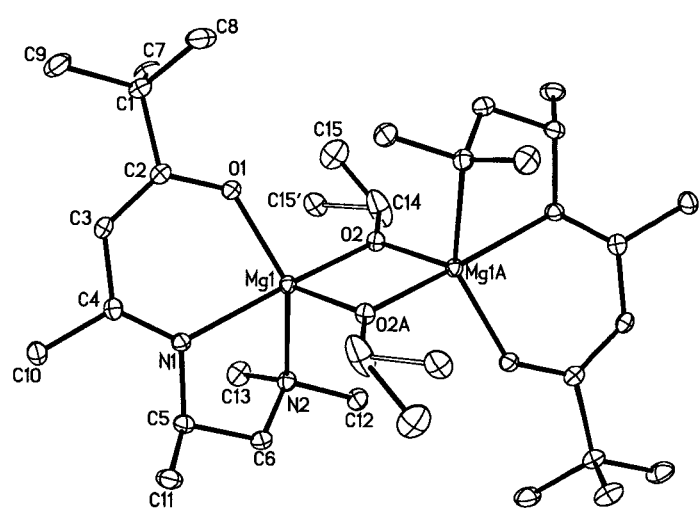
FIG. 3 Crystal structure of (2,2-dimethyl-5(1-dimethylamino-2-propylimino)-3-hexanonato-N,O,N')magnesium ethoxide dimer

The crystal structure of (2,2-dimethyl-5(1-dimethylamino-2-propylimino)-3-hexanonato-N,O,N')magnesium ethoxide dimer was shown in FIG. 3.

(2,2-dimethyl-5(1-dimethylamino-2-propylimino)-3-hexanonato-N,O,N')(ethoxy)magnesium represented structure II(F) with M=magnesium, $R^1=Bu^t$, $R^2=H$, $R^3=Me$, $R^4=$—CH(Me)CH$_2$—, $R^5=R'=Me$, and $R^6=Et$.

Example 3

Synthesis of Bis(2,2-dimethyl-5(1-dimethylamino-2-propylimino)-3-hexanonato-N,O,N')(iso-propoxy)gadolinium To a solution of 0.50 g (1.49 mmol) gadolinium(III)isopropoxide in 15 mL of THF at room temperature was added 0.68 g (2.99 mmol) 2,2-dimethyl-5(1-dimethylamino-2-propylimino)-3-hexanone in 5 mL of THF. Reaction mixture was refluxed for 16 hours after which all volatiles were removed under vacuum. 1.08 g of crystals was isolated after work-up.

Elemental analysis: calcd for $C_{29}H_{57}N_4O_3Gd$: C, 52.22; N, 8.40; H, 8.61. Found: C, 50.21; N, 8.34; H, 8.72.

The structure was confirmed by X-ray single crystal analysis to be bis(2,2-dimethyl-5(1-dimethylamino-2-propylimino)-3-hexanonato-N,O,N')(iso-propoxy)gadolinium.

Bis(2,2-dimethyl-5(1-dimethylamino-2-propylimino)-3-hexanonato-N,O,N')(iso-propoxy)gadolinium represented structure I(A) with M=gadolinium, $R^1=Bu^t$, $R^2=H$, $R^3=Me$, $R^4=$—CH(Me)CH$_2$—, $R^5=R'=Me$, $R^6=Pr^i$, and n=1.

Example 4

Synthesis of Bis(2,2-dimethyl-5(1-dimethylamino-2-propylimino)-3-hexanonato-N,O,N')(iso-propoxy)lanthanum To a solution of 0.50 g (1.58 mmol) lanthanum(III)isopropoxide in 15 mL of THF at room temperature was added 0.72 g (3.16 mmol) 2,2-dimethyl-5(1-dimethylamino-2-propylimino)-3-hexanone in 5 mL of THF. Reaction mixture was refluxed for 16 hours after which all volatiles were removed under vacuum to give 1.16 g of product.

Elemental analysis: $^1$H NMR (500 MHz, $C_6D_6$): δ=5.16 (s, 2H), 4.54 (septet, 1H), 3.80 (t, 2H), 3.45 (m, 2H), 2.49 (b, 6H), 1.97 (b, 6H), 1.80 (dd, 2H), 1.78 (s, 6H), 1.52 (dd, 6H), 1.30 (s, 18H), 1.07 (d, 6H).

Bis(2,2-dimethyl-5(1-dimethylamino-2-propylimino)-3-hexanonato-N,O,N')(iso-propoxy)lanthanum represented structure I(A) with M=lanthanum, $R^1=Bu^t$, $R^2=H$, $R^3=Me$, $R^4=$—CH(Me)CH$_2$—, $R^5=R'=Me$, $R^6=Pr^i$, n=1.

Example 5

Synthesis of Bis(2,2-dimethyl-5(1-dimethylamino-2-propylimino)-3-hexanonato-N,O,N')(iso-propoxy)erbium To a solution of 0.50 g (1.45 mmol) erbium(III)isopropoxide in 15 mL of THF at room temperature was added 0.66 g (2.90 mmol) 2,2-dimethyl-5(1-dimethylamino-2-propylimino)-3-hexanone in 5 mL of THF. Reaction mixture was refluxed for 16 hours after which volatiles were removed under vacuum to provide 1.14 g of product.

Bis(2,2-dimethyl-5(1-dimethylamino-2-propylimino)-3-hexanonato-N,O,N')(iso-propoxy)erbium represented structure I(A) with M=erbium, $R^1=Bu^t$, $R^2=H$, $R^3=Me$, $R^4=$—CH(Me)CH$_2$—, $R^5=R'=Me$, $R^6=Pri$, and n=1.

The working example and embodiments of this invention listed above, are exemplary of numerous embodiments that may be made of this invention. It is contemplated that numerous materials other than those specifically disclosed may be made. Numerous other configurations of the process may also be used, and the materials used in the process may be elected from numerous materials other than those specifically disclosed.

The invention claimed is:

1. A metal-containing complex having a structure I(A):

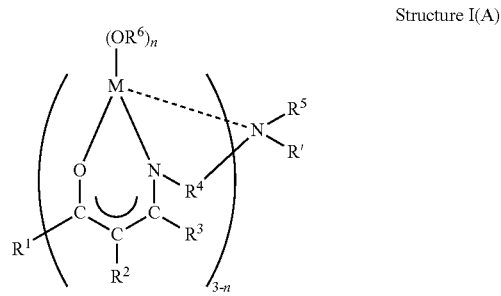

Structure I(A)

wherein $R^1$ is selected from the group consisting of linear or branched alkyl having from 1 to 10 carbon atoms; $R^2$ is selected from the group consisting of hydrogen, alkyl having from 1 to 10 carbon atoms, and aryl having 6 to 10 carbon atoms; $R^3$ is selected from the group consisting of linear or branched alkyl having 1 to 10 carbon atoms and aryl having 6 to 10 carbon atoms; $R^4$ is a linear or branched alkyl bridge having 2 to 10 carbon atoms; $R^5$ and $R^6$ are individually selected from the group consisting of $C_1$-$C_{10}$ linear or branched alkyl; $R^1$ and $R^2$ are optionally connected to form a cyclic group; $R^4$ and $R^5$ are optionally connected to form a cyclic group; R' is selected from the group consisting of C1-10 linear or branched alkyl or alkylsilyl having 3-10 carbon atoms; n=1 or 2; and M is selected from the group consisting of yttrium, lanthanum, gadolinium, erbium, and magnesium.

2. The metal-containing complex of claim 1 having the structure I(A), wherein the linear or branched alkyl is selected from the group consisting of methyl, ethyl, n-propyl, iso-propyl, n-butyl, iso-butyl, sec-butyl, tert-butyl, n-pentyl, iso-pentyl, tert-pentyl, hexyl, octyl, and decyl; and the cyclic group is selected from the group consisting of 5- to 6-membered saturated hydrocarbon ring, 5- to 6-membered hydrocarbon unsaturated ring, and 5- to 6-membered aromatic ring.

3. The metal-containing complex of claim 1 having the structure I(A) selected from group consisting of M=yttrium, $R^1$=Bu$^t$, $R^2$=H, $R^3$=Me, $R^4$=—CH(Me)CH$_2$—, $R^5$=R'=Me, $R^6$=Pr$^i$, and n=1; M=gadolinium, $R^1$=Bu$^t$, $R^2$=H, $R^3$=Me, $R^4$=—CH(Me)CH$_2$—, $R^5$=R'=Me, $R^6$=Pr$^i$, and n=1; M=lanthanum, $R^1$=Bu$^t$, $R^2$=H, $R^3$=Me, $R^4$=—CH(Me)CH$_2$—, $R^6$=R'=Me, $R^6$=Pr$^i$, n=1; and M=erbium, $R^1$=But, $R^2$=H, $R^3$=Me, $R^4$=—CH(Me)CH$_2$—, $R^6$=R'=Me, $R^6$=Pr$^i$, and n=1.

4. The metal-containing complex of claim 1 having the structure I(A), wherein M=Magnesium, $R^1$=Bu$^t$, $R^2$=H, $R^3$=Me, $R^4$=—CH(Me)CH$_2$—, $R^6$=R'=Me, and $R^6$=Et.

5. The metal-containing complex of claim 1 having the structure I(A)

wherein $R^1$ is selected from the group consisting of linear or branched alkyl having from 1 to 5 carbon atoms; $R^2$ is selected from the group consisting of hydrogen, methyl, and ethyl; $R^3$ is a linear or branched alkyl having 1 to 5 carbon atoms; $R^4$ is a linear or branched alkyl bridge having 2 to 4 carbon atoms; $R^1$ and $R^2$ are optionally connected to form a cyclic group; $R^4$ and $R^5$ are optionally be connected to form a cyclic group; $R^5$ and R' are individually selected from the group consisting of a C1-2 alkyl; $R^6$ is selected from the group consisting of C1-5 linear or branched alkyl; and n=1 or 2.

6. A method for producing a film by depositing a precursor comprising the metal containing complex of claim 1 and having the following structure I(A):

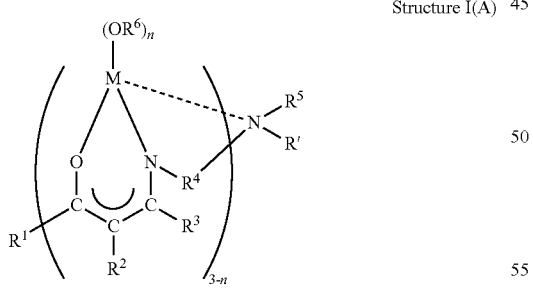

Structure I(A)

wherein $R^1$ is selected from the group consisting of linear or branched alkyl having from 1 to 10 carbon atoms; $R^2$ is selected from the group consisting of hydrogen, alkyl having from 1 to 10 carbon atoms, and aryl having 6 to 10 carbon atoms; $R^3$ is selected from the group consisting of linear or branched alkyl having 1 to 10 carbon atoms and aryl having 6 to 10 carbon atoms; $R^4$ is a linear or branched alkyl bridge having 2 to 10 carbon atoms; $R^5$ and $R^6$ are individually selected from the group consisting of $C_1$-$C_{10}$ linear or branched alkyl; $R^1$ and $R^2$ are optionally connected to form a cyclic group; $R^4$ and $R^5$ are optionally connected to form a cyclic group; R' is selected from the group consisting of C1-10 linear or branched alkyl or alkylsilyl having 3-10 carbon atoms; n=1 or 2; and M is selected from the group consisting of yttrium, lanthanum, gadolinium, erbium, and magnesium.

7. The method of claim 6, wherein the depositing is selected from the group consisting of a chemical vapor deposition (CVD), cyclic chemical vapor deposition (CCVD), plasma enhanced cyclic chemical vapor deposition, an atomic layer deposition (ALD), and plasma enhanced atomic layer deposition.

8. The method of claim 6, wherein the linear or branched alkyl is selected from the group consisting of methyl, ethyl, n-propyl, iso-propyl, n-butyl, iso-butyl, sec-butyl, tert-butyl, n-pentyl, isopentyl, tert-pentyl, hexyl, octyl, and decyl; and the cyclic group is selected from the group consisting of 5- to 6-membered saturated hydrocarbon ring, 5- to 6-membered hydrocarbon unsaturated ring, and 5- to 6-membered aromatic ring.

9. The method of claim 6, wherein the metal-containing complex having the structure I(A), selected from the group consisting of M=yttrium, $R^1$=Bu$^t$, $R^2$=H, $R^3$=Me, $R^4$=—CH(Me)CH$_2$—, $R^5$=R'=Me, $R^6$=Pr$^i$, and n=1; M=gadolinium, $R^1$=Bu$^t$, $R^2$=H, $R^3$=Me, $R^4$=—CH(Me)CH$_2$—, $R^5$=R'=Me, $R^6$=Pr$^i$, and n=1; M=lanthanum, $R^1$=Bu$^t$, $R^2$=H, $R^3$=Me, $R^4$=—CH(Me)CH$_2$—, $R^5$=R'=Me, $R^6$=Pr$^i$, n=1; and M=erbium, $R^1$=But, $R^2$=H, $R^3$=Me, $R^4$=—CH(Me)CH$_2$—, $R^5$=R'=Me, $R^6$=Pri, and n=1.

10. The method of claim 6, wherein the metal-containing complex having the structure I(A), wherein M=Magnesium, $R^1$=Bu$^t$, $R^2$=H, $R^3$=Me, $R^4$=—CH(Me)CH$_2$—, $R^5$=R'=Me, and $R^6$=Et.

11. A multi-component metal oxide film by depositing a precursor comprising the metal containing complex of claim 1 and having the following the structure I(A):

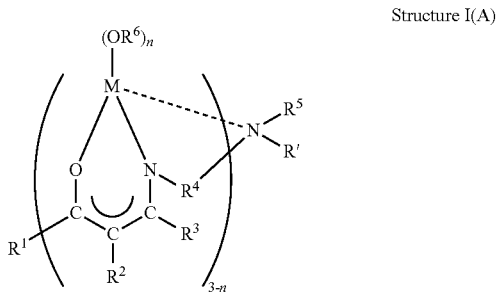

Structure I(A)

wherein $R^1$ is selected from the group consisting of linear or branched alkyl having from 1 to 10 carbon atoms; $R^2$ is selected from the group consisting of hydrogen, alkyl having from 1 to 10 carbon atoms, and aryl having 6 to 10 carbon atoms; $R^3$ is selected from the group consisting of linear or branched alkyl having 1 to 10 carbon atoms and aryl having 6 to 10 carbon atoms; $R^4$ is a linear or branched alkyl bridge having 2 to 10 carbon atoms; $R^5$ and $R^6$ are individually selected from the group consisting of $C_1$-$C_{10}$ linear or branched alkyl; $R^1$ and $R^2$ are optionally connected to form a cyclic group; $R^4$ and $R^5$ are optionally connected to form a cyclic group; R' is selected from the group consisting of C1-10 linear or branched alkyl or alkylsilyl having 3-10 carbon atoms; n=1 or 2; and M is selected from the group consisting of yttrium, lanthanum, gadolinium, erbium, and magnesium.

12. The film of claim 11, wherein the depositing is selected form the group consisting of a chemical vapor deposition (CVD), cyclic chemical vapor deposition (CCVD), plasma enhanced cyclic chemical vapor deposition, an atomic layer deposition (ALD), and plasma enhanced atomic layer deposition.

13. The film of claim 11, wherein the linear or branched alkyl is selected from the group consisting of methyl, ethyl, n-propyl, iso-propyl, n-butyl, iso-butyl, sec-butyl, tert-butyl, n-pentyl, isopentyl, tert-pentyl, hexyl, octyl, and decyl; and the cyclic group is selected from the group consisting of 5- to 6-membered saturated hydrocarbon ring, 5- to 6-membered hydrocarbon unsaturated ring, and 5- to 6-membered aromatic ring.

14. The film of claim 11, wherein the metal-containing complex having the structure I(A), selected from the group consisting of M=Yttrium, $R^1=Bu^t$, $R^2=H$, $R^3=Me$, $R^4=$—CH(Me)CH$_2$—, $R^5=R'=Me$, $R^6=Pr^i$, and n=1; M=gadolinium, $R^1=Bu^t$, $R^2=H$, $R^3=Me$, $R^4=$—CH(Me)CH$_2$—, $R^5=R'=Me$, $R^6=Pr^i$, and n=1; M=lanthanum, $R^1=Bu^t$, $R^2=H$, $R^3=Me$, $R^4=$—CH(Me)CH$_2$—, $R^5=R'=Me$, $R^6=Pr^i$, n=1; and M=erbium, $R^1=But$, $R^2=H$, $R^3=Me$, $R^4=$—CH(Me)CH$_2$—, $R^5=R'=Me$, $R^6=Pri$, and n=1.

15. The film of claim 11, wherein the metal-containing complex having the structure I(A), wherein M=Magnesium, $R^1=Bu^t$, $R^2=H$, $R^3=Me$, $R^4=$—CH(Me)CH$_2$—, $R^5=R'=Me$, and $R^6=Et$.

* * * * *